United States Patent [19]
Fuisz

[11] Patent Number: 5,972,029
[45] Date of Patent: Oct. 26, 1999

[54] REMOTELY OPERABLE STENT

[75] Inventor: Richard C. Fuisz, MacLean, Va.

[73] Assignee: Fuisz Technologies Ltd., Chantilly, Va.

[21] Appl. No.: 09/046,175

[22] Filed: Mar. 23, 1998

Related U.S. Application Data

[63] Continuation-in-part of application No. 08/854,927, May 13, 1997, abandoned.

[51] Int. Cl.$^6$ .................................................. A61F 2/06
[52] U.S. Cl. ................................................. 623/1; 623/12
[58] Field of Search ........................................... 623/1, 12

[56] References Cited

U.S. PATENT DOCUMENTS

| | | | |
|---|---|---|---|
| 4,754,752 | 7/1988 | Ginsburg et al. | 128/303.12 |
| 5,292,321 | 3/1994 | Lee | 606/28 |
| 5,406,158 | 4/1995 | Arnold et al. | 310/692 |
| 5,476,505 | 12/1995 | Limon | 623/1 |
| 5,562,641 | 10/1996 | Flomenblit et al. | 604/281 |
| 5,592,037 | 1/1997 | Sickafus | 310/40 MM |
| 5,676,685 | 10/1997 | Razavi | 606/194 |
| 5,795,318 | 8/1998 | Wang et al. | 604/8 |

OTHER PUBLICATIONS

Mussivand et al. (1995). "A Transcutaneous Energy and Information Transfer System for Implanted Medical Devices," *ASAIO Journal*, vol. 41, pp. M253–M258.

Schuder et al. (1971), "An Inductively Coupled RF System for the Transmission of 1 kW of Power Through the Skin," *IEEE Trans, Biomed. Eng.*, vol. BME–18, pp. 265–273.

Mitamura et al. (1990), "Development of an Implantable Motor–Driven Assist Pump System,"*IEEE Trans. Biomed. Eng.*, vol. 37, pp. 146–156.

*Primary Examiner*—David H. Willse
*Assistant Examiner*—Suzette J. Jackson
*Attorney, Agent, or Firm*—Richard D. Schmidt

[57] ABSTRACT

A remotely operable stent is disclosed which is radially expandable and contractable along the longitudinal length of the stent. Once the stent is positioned within a body lumen requiring radial support, an actuator and expansion/contraction element increase the radial dimension of the stent along the stent's longitudinal length to provide such support. The stent is remotely operable in vivo using a remote activation system such that the radial dimension of the stent can be changed without the need to re-enter the body lumen.

5 Claims, 2 Drawing Sheets

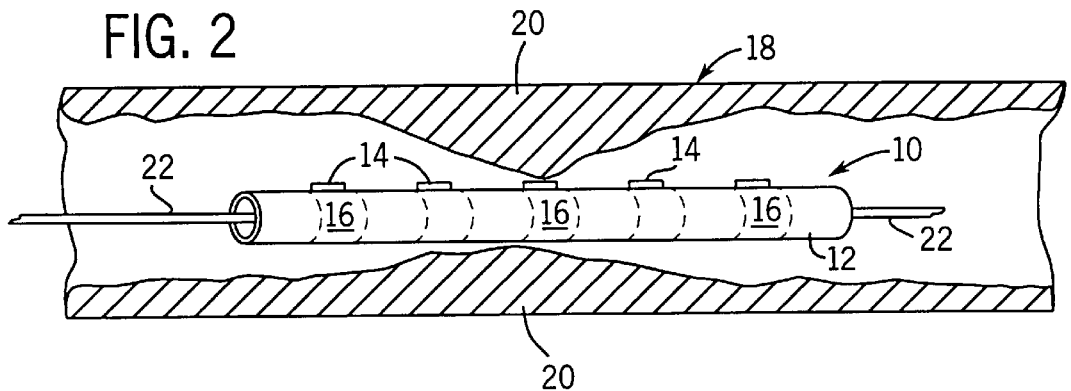
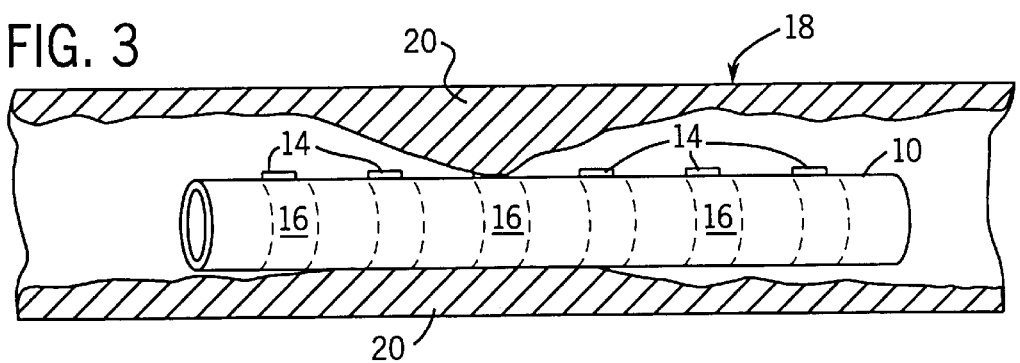
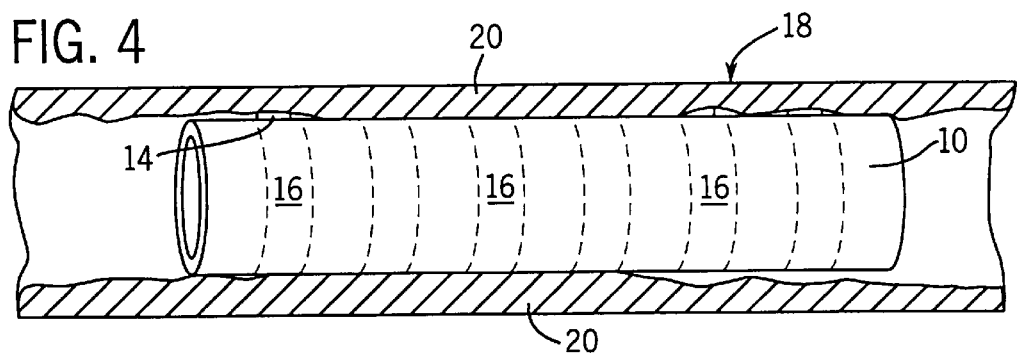

REMOTELY OPERABLE STENT

This application is a continuation-in-part of U.S. application Ser. No. 08/854,927, filed May 13, 1997, now abandoned.

FIELD OF THE INVENTION

The present invention relates to medical stents and more specifically to a stent that is expandable and contractable via remote means after insertion in vivo.

BACKGROUND OF THE INVENTION

In many clinical situations, a lumen in a human or animal body, such as a blood vessel or a urinary tract, can require internal support to ensure proper fluid flow. Support for a lumen can be provided by implantation of a stent in the lumen, which can maintain the radial integrity of the lumen.

A stent is typically a tubular metallic or polymeric body, which is carried on a dilatation catheter to a specific vascular location. The implantation of a stent to maintain patency of a body lumen is well known in the art. In one cardiovascular application, a stent is mounted on a balloon catheter and positioned at the appropriate site within an artery. The balloon is dilated to expand the stent against the vascular wall. The balloon is thereafter deflated and removed, leaving the expanded stent in place in the artery. Due to the structural integrity of the stent, the arterial wall is supported by the stent and prevented from recollapsing. An example of this method is described in U.S. Pat. No. 5,292,321 which is herein incorporated by reference. The stent may also be expandable via thermal energy through the use of electrical activation or radio-frequency electromagnetic irradiation, as described in U.S. Pat. No. 5,562,641.

Several difficulties are associated with the positioning and use of the above-identified stents. For example, it is difficult to simultaneously maintain the radial rigidity and the longitudinal flexibility of the stent to facilitate proper stent delivery. Additionally, the rapid expansion of the stent by such methods can injure the lumen to be protected, often leading to restenosis in the vessel lumen. Ideally, a stent would be expanded slowly over a prolonged period of time to reduce the likelihood of such injury and resulting restenosis.

Furthermore, it has been discovered that over time the movement, activity and changing medical condition of a patient can adversely affect stent operation and/or dictate that a previously expanded stent be further expanded to continue and/or augment the beneficial support provided by the stent. Currently used stents are not capable of prolonged expansion since they are not expandable in vivo, after removal of the positioning catheter; similarly, stent expansion after removal of the positioning catheter cannot be accomplished without re-entry into the lumen.

Accordingly, there remains a need in the art for a stent that can be remotely expanded or contracted in vivo over a prolonged period of time.

SUMMARY OF THE INVENTION

The present invention is directed towards a stent that is remotely expandable or contractable in vivo over a prolonged period of time following stent implantation.

The stent of the present invention comprises a radially cylindrical body portion. Located at one or more locations along its longitudinal length is one or more actuators drivingly associated with one or more expansion/contraction elements that serve to expand or contract the stent's diameter. In a preferred embodiment, the stent is manufactured and sized such that in a completely relaxed state (i.e., when no radial pressure is exerted on the main body of the stent) the stent is at its largest radial dimension. When the one or more expansion/contraction elements are activated by means of one or more signals to the one or more actuators, the main body is reduced/increased in radial dimension in direct proportion to the amount of pressure exerted by the activation of the expansion/contraction elements.

In another embodiment of the present invention, the stent is manufactured and sized such that in a completely relaxed state the stent exhibits its smallest radial dimension. In this embodiment the one or more expansion/contraction elements apply radial pressure from within the main portion of the stent. When the expansion/contraction elements are actuated by means of one or more signals received by the one or more actuators, the main body is increased/reduced in radial dimension in direct proportion to the amount of pressure exerted by the activation of the expansion/contraction elements.

In both of the above-identified embodiments, the one or more expansion/contraction elements are remotely operable by the activation of one or more actuators by any one of a number of remote means such as electromagnetic radiation, including radio frequency (RF) energy and infrared remote activation and control systems.

In use, the remotely operable stent of the present invention is prepared for insertion into the body lumen requiring physical radial support by adjusting the size of the main body of the stent. If the embodiment includes the stent manufactured and sized to have its largest radial dimension when in a completely relaxed state, this is accomplished by actuating the actuator(s) which in turn drive, or activate the expansion/contraction elements to apply radial pressure to the external surface of the main body of the stent, thus reducing the radial dimension of the stent. This reduction is continued until the radial dimension of the stent is small enough to allow the stent to pass through the path of the body lumen and to be positioned appropriately, at which point the activation signals are terminated. In the second embodiment, when the stent is manufactured and sized to have its smallest radial dimension when in a completely relaxed state, the natural state of the stent is appropriate for insertion and thus actuation of the one or more actuators drivingly associated with the expansion/contraction is not required.

Once positioned within the body lumen, the main body of the stent is expanded or contracted by transmitting the activation signal(s) to the actuator(s) which control the expansion/contraction elements to remove or add radial pressure and thereby to provide more or less radial support. The main body of the stent is expanded to its initial configuration (i.e., either slightly expanded, or alternatively, expanded to its fill radial dimension), depending upon the needs of the patient, the condition of the body lumen requiring support and other factors.

Once the remotely operable stent of the present invention is in the initial configuration, the insertion procedure is completed. Subsequently, unlimited adjustments to the stent's initial configuration can be accomplished via remote means, without additional invasive means. Accordingly, the stent can be incrementally expanded over a prolonged period of time to reduce the chance of injury or rupture to the lumen to be supported. Additionally, as the activity and/or condition of the patient warrants, adjustments to the stent's initial configuration can be made without the need to re-enter or otherwise access the lumen.

BRIEF DESCRIPTION OF THE DRAWINGS

For a more complete understanding of the present invention and the advantages thereof, reference is now made to the following description taken in conjunction with the accompanying drawings in which:

FIG. 2 is a side view, partially in section, of the remotely operable stent of the present invention within a body lumen including stenosis;

FIG. 3 is a side view, partially in section, of the remotely operable stent of the present invention having an initial configuration within a body lumen;

FIG. 4 is a side view, partially in section, of the remotely operable stent of the present invention within a body lumen, in a configuration different than its initial configuration.

DETAILED DESCRIPTION OF THE PREFERRED AND ALTERNATIVE EMBODIMENTS

Figure 1:
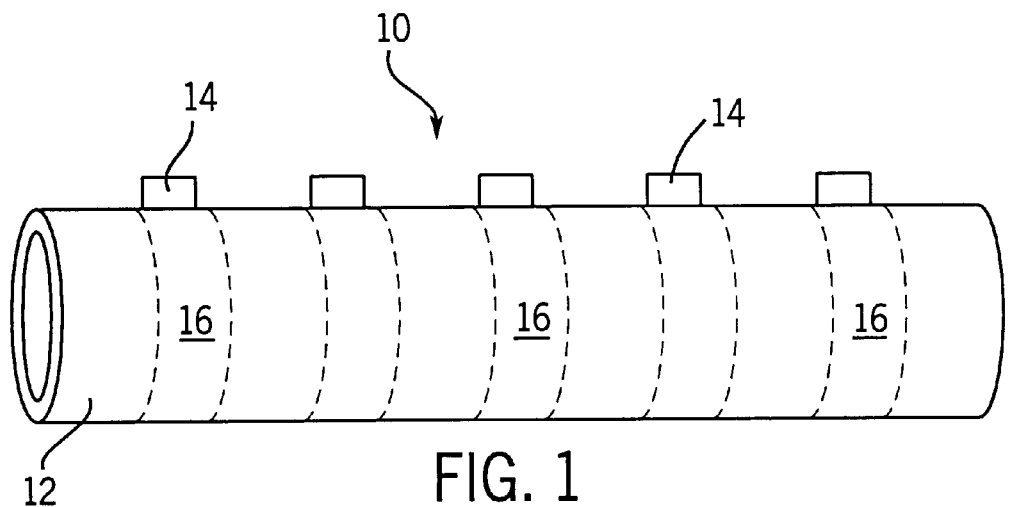
FIG. 1 is a side view of the remotely operable stent of the present invention.

Referring to FIG. 1, there is shown a stent 10 incorporating the features of the preferred embodiment of the present invention. The stent 10 generally comprises a radially cylindrical or tubular main body portion 12 comprising a medical grade, relatively flexible but generally shape-retaining material. Preferred materials include Ni—Ti binary alloy ("nitinol"), Ni—Ti—X (X being V, Co, Cu, Fe) ternary alloy, Cu—Z—Al ternary alloy, and Cu—Al—Ni ternary alloy. Alternatively, the stent can comprise a plastic that is preferably bioabsorbable, biodegradable, biocompatible, non-thrombogenic and sterilizable. The plastic stent is preferably made singly or of a combination of polymers such as polyactide, polyglycolide, polyactide-co-glycolide polydioxanone, polyethylene, polyiminocarbonates, polycaprolactone, polyesters and like materials. Polymeric stents can be provided with relatively fluid impenetrable walls, or porous walls such as to allow drug delivery, as will be apparent to one of skill in the art.

Figure 5:
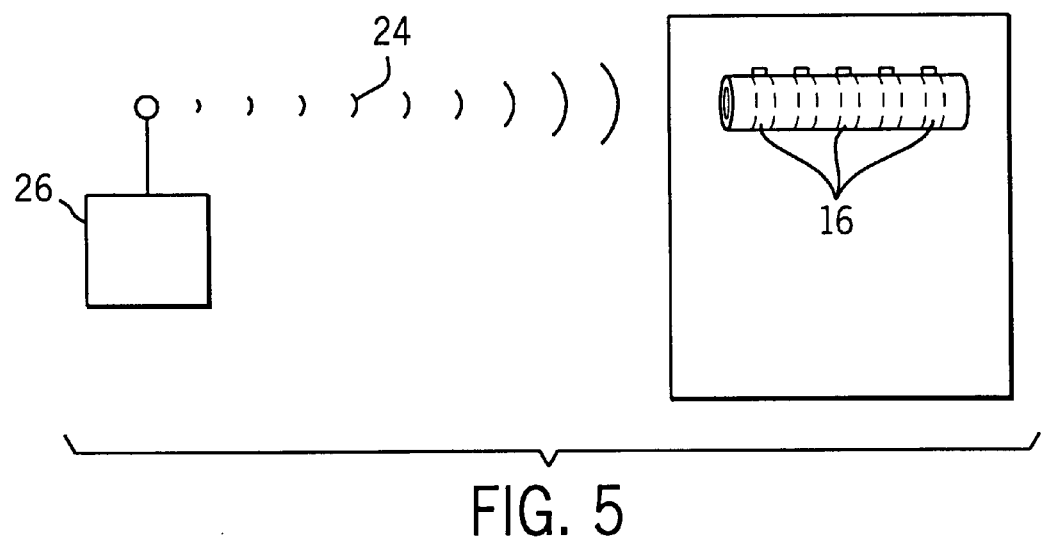
FIG. 5 is a block diagram of the remote activation system.

Located along the longitudinal length of the main body portion 12 are one or more actuators 14. The actuator(s) 14 is drivingly associated with one or more expansion/contraction elements 16 in a manner known in the art, such that the stent is expanded/contracted in response to one or more signals or movements from the one or more actuator(s) which itself is activated in response to one or more signals or other external (outside the lumen) activation processes from an external control source. In a preferred embodiment, a plurality of expansion/contraction elements 16 define bands around the main body 12 that are positioned external to the main body 12. In either embodiment, the one or more actuator(s) 14 are drivingly engaged with one or more of the the expansion/contraction element(s) 16 in a manner known in the art, such as for example, worm gears or other transrotational transfer means. In response to the actuator(s) the expansion/contraction element(s) 16 exert more or less pressure on the main body portion 12 of the stent 10, causing the radial dimension of the main body portion 12 of the stent 10 to increase or decrease. The actuator(s) 14 that drive the expansion/contraction elements 16 are preferably micromotors of a type generally known in the art, drivingly coupled, engaged or otherwise associated therewith. For example, Mussivand, et al. (ASAIO Journal 41 :M253–258, 1995), describe the production of a transcutaneous air-core transformer for use with an implantable ventricular assist device, whereby diaphragm movement of the device is controlled via infrared communications between an external and internal coils. Furthermore, as discussed in U.S. Pat. No. 5,592,037, planar micro-motors and electrically-driven actuators with minimum widths and heights of 20 micrometers or less can be fabricated through the use of well known techniques referred to as microfabrication of miniature devices ("MEMS"), and using well known materials. Referring to FIG. 5, the micro-motor will typically be responsive to an externally generated signal 24, for example an electromagnetic, IR or RF signal, produced by a remote activation system 26, causing actuation of actuator which in turn actuates or drives the expansion/contraction elements 16. Although a micro-motor coupled to an expansion/contraction element is disclosed herein, it is noted that any appropriate actuator may be used, to control the movement of the expansion/contraction elements 16, if desired. It will be obvious to one of ordinary skill in the art that the expansion/contraction elements 16 and the actuator(s) association/coupling can comprise any of the well known devices for translating input energy from the actuator(s) into radial pressure or other useful motion, such as disclosed in U.S. Pat. No. 5,592,037 and in Mussivand, et al.

The main body portion 12 of the stent 10 is generally hollow in nature and is especially flexible along its longitudinal length. In a preferred embodiment of the instant invention, the stent 10 is manufactured and sized such that the stent 10 has its largest radial dimension in its relaxed state (i.e., when none of the expansion/contraction elements 16 are exerting radial pressure on the stent 10). In this embodiment, the expansion/contraction elements 16 apply pressure on the exterior of the main body portion 12 of the stent 10 in respones to activation of the actuators drivingly associated therewith to decrease the radial dimension of the stent 10.

In a further embodiment of the instant invention the stent 10 is manufactured and sized such that such that in a completely relaxed state the stent 10 has its smallest radial dimension. In this embodiment, the expansion/contraction element(s) 16 applies pressure from inside the main body portion 12 of the stent 10 in response to activation of the actuator(s) drivingly associated therewith to increase the radial dimension of the stent 10.

The actuator(s) 14 is controlled remotely via any suitable remote activation and control system, such as electromagnetic or RF energy, infrared and other suitable remote activation and control systems known in the art. By remotely, applicant means the actuator(s) are actuated or activated in response to the activation system or signals in a manner such that the actuator and activation system/signal generator need not be in direct physical or intimate contact. Preferably, the activation system/signal generator is located external to the body cavity into which the stent is implanted. For example, Mossivand, et al. describe an infrared (IR) remote communication system for use with an implantable ventricular assist device. A digital data stream is input into the system using standard transistor transistor logic (TTL) signal levels of 0–5 V. The digital signal is converted into a sinusoidal signal, which is fed into an IR transmitter driver, which converts the electrical signal into a modulating IR light signal directed towards IR receivers on the other side of the skin and tissue barrier. An IR receiver inside the body picks up this IR light signal and converts it back into a sinusoidal data stream, which is then utilized by the ventricular assist device. Similarly, methods for radio frequency transmission of energy into the body via remote means have been described, (Schuder, et al. IEEE Trans. Biomed. Eng. 18:265–273, 1971; Mussivand et al.). It is contemplated that persons skilled in the art can use and adapt these known techniques to design a remote control device to remotely activate the actuator(s) in the stent to cause radial expansion or compression thereof.

As illustrated in FIGS. 2–4, the stent 10 of the present invention is prepared for insertion into a body lumen 18 requiring physical radial support by adjusting the size of the main body 12 of the stent 10. The body lumen 18 illustrated includes an area of stenosis 20 requiring treatment. In the preferred embodiment, the stent 10 is prepared for insertion into the body lumen 18 by actuating the expansion/contraction elements 16 via the actuators 14, so as to apply radial pressure to the main body portion 12 associated therewith, thus reducing the radial dimension of the stent. This reduction is carried out until the longitudinal length of the stent 10 is small enough in radial dimension to allow the stent 10 to pass through the path of the body lumen 18 and be positioned.

In the second embodiment, in which the stent 10 is manufactured and sized to have its smallest radial dimension when in a completely relaxed state, the natural state of the stent 10 exhibits the smallest radial dimension in size and thus no actuation of the expansion/contraction elements 16 by the actuator(s) is required.

The stent 10 is guided into the proper position within the body lumen 18 via a guidewire 22 or like device such as described in U.S. Pat. No. 4,754,752, or as known in the art. Although a guidewire device is disclosed herein, it is noted that the stent 10 can be guided into proper position within a body lumen 18 using any appropriate device, as for example, a catheter system, also described in U.S. Pat. No. 4,754,752.

Now referring to FIG. 3, once the stent 10 is in place within the body lumen 18, the guidewire 22 is removed and the main body portion 12 is expanded to provide radial support to the stenotic area 22 of the body lumen 18. This is accomplished via the remote transmitter sending an RF electromagnetic signal, or other suitable signal, to the actuator 14, which responsively activates the expansion/contraction element 16 to adjust the radial force applied to the main body portion 12 of the stent 10. In the preferred embodiment, as such radial force decreases, the generally shape-retaining nature of the material of the stent 10 naturally expands to increase the radial dimension of the main body portion 12 of the stent 10. Depending upon the needs of the patient, the condition of the body lumen 18 requiring support, and like factors, the main body portion 12 of the stent 10 is expanded slightly or, alternatively, to its full radial dimension to provide the needed radial support. As can be seen in FIG. 4, the stent 10 is configured to provide maximum radial support to the body lumen 18. Once the stent 10 is in the initial configuration (FIG. 3) the insertion procedure is complete. Subsequently, to avoid discomfort to, injury or rupture of the body lumen 18, the stent 10 can be expanded incrementally over a prolonged period of time via the remote activation system, while providing the maximum radial support to the body lumen 18. Additionally, adjustments to the configuration of the stent 10 can be made without re-entering or otherwise invasively accessing the body lumen 18. This feature of the stent 10 allows, for example, a physician or other medical personnel to expand or contract the main body portion 12 of the stent 10 in the event the stent 10 becomes crimped or otherwise adversely affected through activity or changing medical condition without the need for invasive surgical procedures.

The second embodiment described herein operates identically to the preferred embodiment, except that the expansion/contraction elements 16 of the stent 10 of the second embodiment apply radially outward forces from within the main body portion 12 of the stent 10 to increase the stent's radial dimension.

Although preferred embodiments of the invention have been illustrated in the accompanying drawings and described in the foregoing Detailed Description, it will be understood that the invention is not limited to the embodiments disclosed, but is capable of modification without departing from the spirit of the invention.

I claim:

1. A stent remotely and non-invasively adjustable when the stent is implanted in a living animal comprising:
   a tubular body portion defining a longitudinal length, a hollow interior and an exterior surface;
   one or more expansion/contraction elements located along said longitudinal length of said body portion; and
   one or more actuators operatively associated with said one or more expansion/contraction elements, wherein said actuators are remotely responsive to an activation signal from a control source remote from and not in direct physical contact with said one or more actuators for operatively actuating said one or more expansion/contraction elements for increasing or decreasing the radial dimension of said body portion of said stent.

2. A system for remotely controlling the radial dimension of a stent implanted in a living animal, comprising:
   a stent remotely adjustable when the stent is implanted in a living animal comprising:
      a tubular body portion defining a longitudinal length, a hollow interior and an exterior surface;
      one or more expansion/contraction elements located along said longitudinal length of said body portion; and
      one or more actuators operatively associated with said one or more expansion/contraction elements; and
   a control source for transmitting an activation signal, said control source located remote from and external and not in direct physical contact with to said one or more actuators; wherein said actuators are responsive to an activation signal from said remotely located control source; and whereby the expansion and contraction of said stent are remotely adjusted by means of said remotely located control source.

3. The system of claim 2, wherein said control source comprises a source of electromagnetic radiation and means of transmission thereof.

4. The system of claim 2, wherein said source comprises an infrared source.

5. The system of claim 2, wherein said source comprises a radio-frequency energy source.

* * * * *